(12) United States Patent
Bosch et al.

(10) Patent No.: US 7,582,583 B2
(45) Date of Patent: Sep. 1, 2009

(54) SHAPED BODY CONTAINING A MICROPOROUS MATERIAL AND AT LEAST ONE SILICON-CONTAINING BINDER, METHOD FOR THE PRODUCTION THEREOF AND ITS USE AS A CATALYST, PARTICULARLY IN A METHOD FOR PRODUCING TRIETHYLENEDIAMINE (TEDA).

(75) Inventors: Marco Bosch, Mannheim (DE); Matthias Frauenkron, Freinsheim (DE); Milan Kostur, Ludwigshafen (DE); Otto Hofstadt, Speyer (DE)

(73) Assignee: BASF SE, Ludwigshafen (DE)

( * ) Notice: Subject to any disclaimer, the term of this patent is extended or adjusted under 35 U.S.C. 154(b) by 368 days.

(21) Appl. No.: 11/629,889

(22) PCT Filed: Jun. 10, 2005

(86) PCT No.: PCT/EP2005/006242

§ 371 (c)(1),
(2), (4) Date: Dec. 18, 2006

(87) PCT Pub. No.: WO2005/123256

PCT Pub. Date: Dec. 29, 2005

(65) Prior Publication Data

US 2008/0221326 A1 Sep. 11, 2008

(30) Foreign Application Priority Data

Jun. 18, 2004 (DE) .................... 10 2004 029 544

(51) Int. Cl.
*B01J 29/06* (2006.01)
*C07C 209/60* (2006.01)

(52) U.S. Cl. .................. 502/63; 502/64; 564/470; 564/474; 564/479; 564/480

(58) Field of Classification Search ........................ None
See application file for complete search history.

(56) References Cited

U.S. PATENT DOCUMENTS

| | | | |
|---|---|---|---|
| 3,702,886 | A | 11/1972 | Argauer et al. |
| 3,709,979 | A | 1/1973 | Chu |
| 5,053,374 | A | 10/1991 | Absil et al. |
| 5,614,079 | A | 3/1997 | Farnos et al. |
| 5,731,449 | A | 3/1998 | Li et al. |
| 5,741,906 | A | 4/1998 | Santiesteban et al. |
| 6,077,984 | A | 6/2000 | Drake et al. |
| 6,084,096 | A | 7/2000 | Li et al. |
| 6,458,187 | B1 | 10/2002 | Fritz et al. |
| 6,555,688 | B1 | 4/2003 | Klockemann et al. |
| 6,562,971 | B2 | 5/2003 | Frauenkron et al. |
| 6,710,002 | B2 | 3/2004 | Grosch et al. |
| 6,958,397 | B2 | 10/2005 | Frauenkron et al. |
| 2002/0072467 | A1 | 6/2002 | Tosoh Corporation |
| 2002/0107394 | A1 | 8/2002 | Frauenkron et al. |
| 2003/0139598 | A1 | 7/2003 | Frauenkron et al. |
| 2006/0046929 | A1 | 3/2006 | Hofstadt et al. |
| 2006/0116517 | A1 | 6/2006 | Bosch et al. |

FOREIGN PATENT DOCUMENTS

| | | |
|---|---|---|
| DE | 197 23 949 A1 | 12/1998 |
| DE | 198 26 209 A1 | 12/1999 |
| DE | 102 19 879 A1 | 11/2003 |
| DE | 103 26 137 A1 | 12/2004 |
| DE | 103 56 184 A1 | 7/2005 |
| EP | 0130407 | 1/1985 |
| EP | 0 349 859 A2 | 1/1990 |
| EP | 0 382 055 A1 | 8/1990 |
| EP | 0 712 662 A2 | 5/1996 |
| EP | 0 831 096 A2 | 3/1998 |
| EP | 831096 | 3/1998 |
| EP | 0842936 | 5/1998 |
| EP | 0 952 152 A2 | 10/1999 |
| EP | 1 053 786 A1 | 11/2000 |
| EP | 1 192 993 A1 | 4/2002 |
| EP | 1 215 211 A1 | 6/2002 |
| JP | 3132061 | 6/1991 |
| JP | 5017460 | 1/1993 |
| JP | 5017461 | 1/1993 |

(Continued)

OTHER PUBLICATIONS

Huber, G. et al., "Hydrothermal Stability of Co/SiO2 Fischer-Tropsch Synthesis Catalysts", Studies in Surface Science and Catalysis, Elsevier, 139 (2001), p. 423-430.
Ullman's Encyclopedia of Industrial Chemistry, 6th Edition, 2000 Electronic Release, Chapter 3.2.
Ullmann's Encyclopedia of Industrial Chemistry, 6th Edition, 2000 Electronic Release, Chapter 6.3.2.
Ullmann's Encyclopedia of Industrial Chemistry, 6th Edition, 2000 Electronic Release, Chapter 7.6.
Ullmann's Encyclopedia of Industrial Chemistry, 6th Edition, 2000 Electronic Release, Chapter 8.3.2.

(Continued)

*Primary Examiner*—Brian J Davis
(74) *Attorney, Agent, or Firm*—Connolly Bove Lodge & Hutz LLP

(57) ABSTRACT

Process for producing a shaped body comprising a microporous material and at least one silicon-containing binder, which comprises the steps
(I) preparing a mixture comprising the microporous material, the binder, a make-up aid and a solvent,
(II) mixing and densifying the mixture,
(III) shaping the densified mixture to give a shaped body,
(IV) drying the shaped body and
(V) calcining the dried shaped body,
wherein the binder used is an organosilicon compound, shaped bodies which can be produced by this process, their use as catalyst, in particular in organic synthesis and very particularly preferably in a process for preparing triethylenediamine (TEDA).

41 Claims, No Drawings

FOREIGN PATENT DOCUMENTS

| | | |
|---|---|---|
| JP | 5017462 | 1/1993 |
| WO | WO 91/04943 | 4/1991 |
| WO | WO-98/55228 A1 | 12/1998 |
| WO | WO-01/02404 A2 | 1/2001 |
| WO | WO-01/23089 A1 | 4/2001 |
| WO | WO 02086946 | 10/2002 |
| WO | WO-03/004499 A1 | 1/2003 |
| WO | WO-2005/053842 A1 | 6/2005 |

OTHER PUBLICATIONS

W.T. Reichle, "Reactions of Aliphatic a-w-Diamines in H+-Pentasils", Journal of Catalysis 144, pp. 556-568 (1993).

International Preliminary Report on Patentability, Chapter II, for International Application PCT/EP2005/006242, issued Mar. 1, 2007.

Weitkamp, J. et al. (Editors), Catalysis and Zeolites, Fundamentals and Applications, Springer Verlag, Chapter 3.3.3.3, pp. 142-144, 1999.

SHAPED BODY CONTAINING A MICROPOROUS MATERIAL AND AT LEAST ONE SILICON-CONTAINING BINDER, METHOD FOR THE PRODUCTION THEREOF AND ITS USE AS A CATALYST, PARTICULARLY IN A METHOD FOR PRODUCING TRIETHYLENEDIAMINE (TEDA).

CROSS-REFERENCE TO RELATED APPLICATIONS

This application is a National Stage of PCT Application PCT/EP2005/006242 filed Jun. 10, 2005 which in turn claims priority from German Application 10 2004 029 544.1, filed Jun. 18, 2004 disclosures of which are incorporated herein by reference.

The present invention relates to a shaped body comprising a microporous material and at least one silicon-containing binder, a process for producing it which comprises the steps
(I) preparing a mixture comprising the microporous material, the binder, a make-up aid and a solvent,
(II) mixing and densifying the mixture,
(III) shaping the densified mixture to give a shaped body,
(IV) drying the shaped body and
(V) calcining the dried shaped body, and its use as catalyst, in particular in the process for preparing triethylenediamine (TEDA).

TEDA (IUPAC name: 1,4-diazabicyclo[2.2.2]octane) is an important intermediate and end product in the chemical industry and is used mainly as such as catalyst in polyurethane production.

To prepare triethylenediamine (TEDA), there is a large number of different syntheses which differ mainly in the choice of starting materials and the catalysts employed.

It is known that TEDA can be prepared by gas-phase reaction of one or more of the amine compounds ethylenediamine (EDA), monoethanolamine (MEOA), diethanolamine, triethanolamine, piperazine (PIP), diethylenetriamine, triethylenetetramine, tri(2-aminoethyl)amine, N-(2-aminoethyl)ethanolamine, morpholine, N-(2-hydroxyethyl)piperazine, N,N'-bis(2-hydroxyethyl)piperazine, N-(2-aminoethyl)piperazine or N,N'-bis(2-aminoethyl)piperazine over heterogeneous acid catalysts.

In the commercial processes for preparing TEDA, a distinction can be made between two types of catalyst.

The classical process uses alkali metal phosphate and alkaline earth metal phosphate catalysts. As an alternative, a zeolite-catalyzed process can be utilized.

In phosphate catalysis, it is mainly piperazine, N-(2-hydroxyethyl)piperazine and N,N'-bis(2-hydroxyethyl)piperazine which are reacted. The selectivity to TEDA is up to 85% (Air Products, EP-A1-1 053 786).

In the case of zeolite catalysis, N-(2-aminoethyl)piperazine (Tosoh Corp., JP-B-3 132 061, JP-B-3 132 062, JP-B-3 132 063 and EP-A1-1 192 993), ethylenediamine and/or piperazine (Air Products, EP-A1-842 936; BASF AG, EP-A1-382 055, WO 01/02404, EP-A1-1 215 211 and WO-A-03/004499) are mainly used as starting materials. Selectivities to TEDA of up to 90% can be achieved in such a process.

The earlier German patent application no. 10326137.0 of Jun. 6, 2003 (BASF AG) relates to a method of increasing the cutting hardness of a shaped body comprising a crystalline aluminosilicate and chemical syntheses in the presence of a crystalline aluminosilicate catalyst, in particular a process for preparing triethylenediamine (TEDA) by reaction of ethylenediamine (EDA) and/or piperazine (PIP).

Zeolites are, as is known, crystalline aluminosilicates having ordered channel and cage structures containing micropores which are preferably smaller than about 0.9 nm. The network of such zeolites is built up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolithe Structure Types", El-sevier, 5th Edition, Amsterdam 2001.

Specific mention may be made of, for instance, zeolites of the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures of two or more of the abovementioned structures, in particular zeolites having a pentasil structure.

Depending on the use to which the catalyst is put, it should or has to have not only a particular crystal size but also a particular pore size or pore distribution. For example, the use of a zeolitic catalyst of the structure type ZSM-5 has been found to be useful in the preparation of triethylenediamine. Apart from the above-described properties, the catalyst should or has to also have a particular chemical composition. In the case of the ZSM-5 catalyst, for example, a molar ratio of Si to Al in the zeolitic material within particular ranges is advantageous.

The use of a zeolite catalyst of the structure type ZSM-5 in the preparation of triethylenediamine is described, for example, in WO-A-01/02404, with the molar ratio of Si to Al being in the range from 100 to 700, particularly preferably in the range from 150 to 250.

WO-A-03/004499 describes a process for the selective synthesis of triethylenediamine, in which a zeolite catalyst, in particular of the ZSM-5 type, having a molar ratio of Si to a metal M in the range above 100, preferably above 200, more preferably from >300 to 40 000 and particularly preferably from 400 to 5000, is used. The metal M, which can occur in the oxidation state III or IV, is selected from the group consisting of Al, B, Fe, Co, Ni, V, Mo, Mn, As, Sb, Bi, La, Ga, In, Y, Sc, Cr and mixtures thereof or Ti, Zr, Ge, Hf, Sn and mixtures thereof. Particular preference is given to an aluminosilicate.

EP-A1-1 215 211 describes a process for preparing triethylenediamine, in which a zeolite catalyst comprising one or more metals M in the oxidation states II, III or IV as oxides is used as catalyst, where, when M is Al, the molar ratio of $SiO_2$ to $Al_2O_3$ is greater than 1400. Apart from ZSM-5, further catalysts of the structure type ZSM-11, ZSM-23, ZSM-53, NU-87, ZSM-35 and mixed structures are disclosed.

The earlier German patent application no. 10356184.6 of Dec. 2, 2003 (BASF AG) relates to a zeolitic material of the pentasil structure type, in particular of the structure type ZSM-5, having an alkali metal and alkaline earth metal content of not more than 150 ppm and a molar ratio of Si to Al in the range from 250 to 1500, in which at least 95% by weight of the spherical primary particles of the zeolitic material have a diameter in the range below or equal to 1 µm and at least 95% of all primary particles are spherical. That application likewise relates to a shaped body comprising this zeolitic material and the use of the zeolitic material itself or of the shaped body as catalyst, in particular in the synthesis of TEDA.

The use of colloidal silica as $SiO_2$ binder for producing shaped catalyst bodies is described in "Catalyst Support and Supportes Catalysts" (A. B. Stiles), 1987, Chapter 1, on pages 1 to 9 and in Chapter 3 on pages 57 to 62, in "Applied Heterogeneous Catalysis—Design, Manufacture, Use Of Solid Catalysts" (J.-F. Lepage, J. Cosyns, P. Courty, E. B. Miller), 1987, Chapter 5, on pages 75 to 123, in "Heterogeneous Catalysis In Industrial Practice" (C. N. Satterfield), 2nd Edition, 1991, Chapter 4, on pages 87 to 130 and especially on page 121, and in "Studies in Surface Science and Catalysis" (E. B. M. Doesburg, J. H. C. Hooff), 1993, Chapter 8 on pages 309 to 332.

The use of colloidal silica and especially Ludox® AS40 from DuPont as $SiO_2$ binder for the shaping of ZSM-5 powder is described in U.S. Pat. No. 6,077,984.

WO-A-01/23089 describes the production of shaped catalyst bodies comprising a ZSM-5 powder and an $SiO_2$ binder and having cutting hardnesses of greater than 1 kg. Colloidal silica is used as $SiO_2$ binder.

EP-A1-831 096 describes the role of the binder in the catalytic preparation of TEDA over ZSM-5 catalysts. The use of a matrix (=binder) having an acidity lower than that of silica and zirconia is said to suppress undesirable secondary reactions.

EP-A1-349 859 describes ZSM-5 catalysts for the preparation of TEDA from EDA/PIP mixtures, which catalysts have been shaped using finely divided silica as binder. Auxiliaries which can be used for extrusion include, inter alia, ethylcellulose, stearic acid, potato starch and silicon-containing esters.

EP-A1-1 192 993 relates to a process for preparing TEDA over shaped catalyst bodies comprising
a) a crystalline aluminosilicate having a molar ratio of silica to alumina of at least 12 in a proportion of from 30 to 95% by weight,
b) an amorphous silica in a proportion of from 5 to 70% by weight, and having
c) a cutting hardness of the shaped bodies of at least 1 kg.

Shaping comprises mixing and densifying amorphous silica and the aluminosilicate in a mechanical mixer, optionally in the presence of water, and obtaining the shaped bodies by shaping in a shaping apparatus. The amorphous silica has primary particles having an average diameter of from 6 to 60 nm.

The use of silicon-containing compounds for passivating the outer zeolite surface of ZSM-5 catalysts and improving the selectivity in the preparation of TEDA is described in EP-A1-0 952 152. The passivation by means of the silicon-containing compound is independent of the shaping step using a binder, which is preferably silica. As silicon-containing compounds for passivating the zeolite surface, tetraalkyl orthosilicates, in particular tetraethyl orthosilicate, silica gels and polysiloxanes are specifically claimed.

DE-A1-102 19 879 relates to a process for producing a catalyst support, in which zirconium dioxide powder is shaped together with a binder to form shaped bodies, dried and calcined, with the binder being a monomeric, oligomeric or polymeric organosilicon compound. The patent application also relates to the catalyst support produced in this way itself, a catalyst comprising this support and its use as dehydrogenation catalyst.

In the field of catalysts in particular, it is often desirable to use not the crystalline, catalytically active material as such for reactions but instead the material present in shaped bodies. These shaped bodies are necessary in many industrial processes, for example to make it practical to carry out chemical reactions in, for example, tube reactors or shell-and-tube reactors, e.g. in the fixed-bed mode.

It is known that catalysts and in particular zeolite catalysts having an $SiO_2$ binder can be obtained by shaping with the aid of colloidal silica. The use of colloidal silica for the shaping of zeolite catalysts for the preparation of TEDA is preferred because it has a low acidity and the formation of by-products is accordingly suppressed (EP-A1-0 831 096; cf. above).

It has been recognized according to the invention that the mechanical stability of shaped catalyst bodies comprising a microporous, in particular zeolitic, material and at least one silicon-containing binder for use on an industrial scale is capable of improvement, particularly when the primary particles of the microporous, in particular zeolitic, material are small and spherical (e.g. smaller than 1 µm in diameter) and/or when shaping to produce shaped catalyst bodies is carried out using commercially available colloidal silica (e.g. Ludox®).

It was an object of the present invention to provide improved shaped bodies which comprise a microporous, in particular zeolitic, material and at least one silicon-containing binder and can be used as catalysts and have improved mechanical stability, e.g. measured as cutting hardness (in newton (N)), e.g. a cutting hardness of greater than or equal to 10 N.

The shaped bodies used as catalysts in chemical reactions, in particular in the synthesis of TEDA, should also make improved conversions and space-time yields, higher selectivities and longer operating lives possible.

When they are used in the synthesis of TEDA, the TEDA selectivity should be greater than 90%, in particular up to 95%, and a long operating life (e.g. >2500 h) should be achieved even at a low proportion of water in the feed (e.g. less than 90% by weight based on the starting material).

("Starting material" comprises one or more amines having a structural unit of the formula I, cf. the process claims and the description below relating to the preparation of TEDA).

These advantageous properties should very particularly preferably be obtained in the case of shaped bodies which comprise a zeolitic material and at least one silicon-containing binder and in which at least 90% of the primary particles of the zeolitic material are spherical and at least 95% by weight of the spherical primary particles have a diameter of less than or equal to 1 µm.

It has surprisingly been found that shaping of a microporous material, in particular a zeolitic material (e.g. a zeolite powder), together with an organosilicon compound (e.g. a silicone) as binder can be successfully carried out and leads to shaped bodies whose mechanical properties (in particular the cutting hardness) is clearly superior to the shaped bodies shaped using colloidal silica, without this improved mechanical stability having an adverse effect on the selectivity and/or activity of the shaped body as catalyst, e.g. in the preparation of triethylenediamine (TEDA).

We have accordingly found a process for producing a shaped body comprising a microporous material and at least one silicon-containing binder, which comprises the steps
(I) preparing a mixture comprising the microporous material, the binder, a make-up aid and a solvent, (II) mixing and densifying the mixture,
(III) shaping the densified mixture to give a shaped body,
(IV) drying the shaped body and
(V) calcining the dried shaped body, wherein the binder used is an organosilicon compound.

Furthermore, we have found the shaped bodies which can be produced by this process, their use as catalyst, in particular in organic synthesis, very particularly in a process for preparing triethylenediamine (TEDA).

The Organosilicon Compound as Binder (Step I)

Suitable organosilicon binders include monomeric, oligomeric or polymeric silanes, alkoxysilanes, acyloxysilanes, oximinosilanes, halosilanes, aminoxysilanes, aminosilanes, amidosilanes, silazanes or silicones, as are described, for example, in Ullmann's Encyclopedia of Industrial Chemistry, Vol. A24, on pages 21 to 56, and in Lehrbuch der Anorganischen Chemie (A. F. Holleman, E. Wiberg), 100th Edition, Chapter 2.6.5, on pages 786 to 788. In particular, they include the monomeric compounds of the formulae (A) to (F) as follows:

$(Hal)_x SiR_{4-x}$     (A)

$(Hal)_x Si(OR)_{4-x}$     (B)

$(Hal)_x Si(NR^1 R^2)_{4-x}$     (C)

$R_x Si(OR^1)_{4-x}$     (D)

$R_x Si(NR^1 R^2)_{4-x}$     (E)

$(RO)_x Si(NR^1 R^2)_{4-x}$     (F)

where
the radicals Hal are each, independently of one another, halogen (F, Cl, Br or I, in particular Cl),
R, $R^1$, $R^2$ are each, independently of one another, H or an optionally substituted alkyl, alkenyl, alkynyl, cycloalkyl, cycloalkenyl, arylalkyl or aryl radical, and
x is an integer in the range from 0 to 4.

Among alkyl radicals, $C_{1-6}$-alkyl radicals are preferred. They can be linear or branched. Preferred examples are methyl, ethyl, n-propyl, n-butyl, sec-butyl and tert-butyl, especially methyl or ethyl.

As aryl radicals, preference is given to $C_{6-10}$-aryl radicals, for example phenyl.

Preferred arylalkyl radicals are $C_{7-20}$-arylalkyl radicals, in particular benzyl.

Preferred alkenyl radicals are $C_{2-6}$-alkenyl radicals, in particular vinyl or allyl.

As alkynyl radicals, preference is given to $C_{2-6}$-alkynyl radicals, for example ethynyl or propargyl.

Among acyl radicals, preference is given to $C_{2-6}$-acyl radicals, in particular an acetyl radical.

Preferred cycloalkyl radicals are $C_{5-8}$-cycloalkyl radicals, in particular cyclopentyl or cyclohexyl.

Preferred cycloalkenyl radicals are $C_{5-8}$-cycloalkenyl radicals, for example 1-cyclopentenyl or 1-cyclohexenyl.

Examples of suitable organosilicon compounds of the formula (A) are $MeSiCl_3$, $Me_2SiCl_2$, $Me_3SiCl$, and $Me_4Si$. Further, formula (A) may be $SiCl_4$.

Examples of suitable organosilicon compounds of the formula (B) are $Si(OMe)_4$, $ClSi(OMe)_3$, $Cl_2Si(OMe)_2$, $Cl_3SiOMe$. (Me=methyl)

Examples of suitable organosilicon compounds of the formula (C) are $Si(NMe_2)_4$, $ClSi(NMe_2)_3$, $Cl_2Si(NMe_2)_2$, $Cl_3SiNMe_2$.

Suitable organosilicon compounds of the formula (D) are, for example, $Si(OEt)_4$, $MeSi(OEt)_3$, $Me_2Si(OEt)_2$ and $Me_3Si(OEt)$.

Suitable compounds of the formula (E) are, for example, $Me_3Si(N(Me)COMe)$ and $Me_3Si(N(Me)COCH_2C_6H_5)$.

A suitable compound of the formula (F) is, for example, $(MeO)_3Si(NMe_2)$.

Preference is given to using a cyclic silicone of the formula [—SiO(OR)(R')—]$_x$ or a linear silicone of the formula RO—[SiO(OR)(R')—]$_x$—R or a mixture of these silicones, where R and R' are (independently of one another) $C_{1-6}$-alkyl groups (as defined above), in particular methyl, ethyl, and x is from 2 to 50, in particular from 3 to 20, as binder.

Very particularly preferred organosilicon binders are methylsilicones, for example the Silres® grades from Wacker, e.g. Silres® MSE100.

Shaping is preferably carried out using halogen-free organosilicon binders in order to avoid corrosion during the preparation of the shaped bodies or when the shaped bodies are used in the catalytic reaction.

The organosilicon compounds used as binders are preferably liquid under normal conditions or are used as a solution in a preferably nonpolar organic solvent such as hexane, toluene and/or cyclohexane. As a result, the high-surface-area microporous active component is uniformly wetted with the organosilicon compound on mixing. During calcination of the shaped catalyst bodies, the organic radicals of the organosilicon binder burn. This forms $SiO_2$ which is present in very finely divided form in the shaped body. This results in strong bonding between the primary particles of the microporous active component and a very good mechanical stability of the shaped catalyst bodies obtained. The combustion of the organic radicals of the organosilicon binder forms additional pores. Owing to the uniform distribution of the organosilicon binder in the shaped body, these pores are likewise very uniformly distributed. This increases the total porosity of the catalyst support.

It is preferred that at least 80% by weight, in particular at least 95% by weight, of the organosilicon compound is converted into finely divided $SiO_2$ by the calcination of the shaped bodies in step V. The proportion by weight of the resulting finely divided $SiO_2$ in the finished shaped catalyst body is preferably in the range from 5 to 70% by weight, in particular in the range from 10 to 50% by weight, very particularly preferably in the range from 10 to 30% by weight.

The Microporous, in Particular Zeolitic, Material (Step I)

The microporous material is preferably a crystalline silicalite, a crystalline aluminosilicate (=zeolitic material), a crystalline silicoaluminophosphate and/or a crystalline aluminophosphate. Preference is given to crystalline aluminosilicates, especially zeolites. The zeolite is preferably a pentasil and preferably has one of the structure types MFI, MEL or a mixed structure derived therefrom.

Very particular preference is given to zeolites of the pentasil structure type, e.g. ZSM-5, having a total alkali metal and alkaline earth metal content of not more than 150 ppm by weight and in particular a molar ratio of Si to Al of greater than 10, particularly in the range from 100 to 5000, preferably in the range from 250 to 1500, particularly preferably in the range from 250 to 750.

The microporous material used in (I) is preferably at least partly in the $H^+$ and/or $NH_4^+$ form. Particular preference is given to at least part of the microporous material used in (I) being employed in the $H^+$ form and very particular preference is given to more than 95% being employed in the $H^+$ form.

In a preferred embodiment, at least 90% by weight of the primary particles of the zeolitic material are spherical and, in particular, at least 95% by weight of the spherical primary particles have a diameter in the range below or equal to 1 µm.

The term "spherical" as used for the purposes of the present invention refers to primary particles which are essentially free of sharp edges when examined by scanning electron microscopy (SEM) at a magnification in the range from $0.5 \cdot 10^4$ to $2.0 \cdot 10^4$. Accordingly, the term "spherical" refers, for example, to purely spherical primary particles or deformed spherical, for example elliptical, or cuboidal primary particles, where in the case of the cuboidal primary particles the edges are rounded and not sharp when examined by the abovementioned method in the specified resolution range.

The term "structure type ZSM-5" as is used for the purposes of the present invention refers to a zeolitic material as described in W. M. Meier, D. H. Olson and Ch. Baerlocher, "Atlas of Zeolithe Structure Types", Elsevier, 5th Edition, Amsterdam 2001, pp. 184-185, as a zeolite of the structure type ZSM-5.

The primary particles of the zeolitic material preferably have diameters of less than 1 µm. Greater preference is given to diameters of not more than 900 nm, more preferably not more than 800 nm, more preferably not more than 700 nm, more preferably not more than 600 nm and particularly preferably not more than 500 nm. Furthermore, the primary particles of the zeolitic material preferably have a diameter in the range of at least 10 nm, more preferably at least 20 nm, more preferably at least 30 nm, more preferably at least 40 nm and particularly preferably at least 50 nm. The diameters are particularly preferably in a range from 50 to 500 nm, more particularly preferably from 50 to 400 nm, more particularly preferably from 50 to 300 nm, more particularly preferably from 50 to 250 nm and very particularly preferably from 50 to 200 nm.

In a further embodiment of the present invention, the diameter can also be in the range from 50 to 100 nm or in the range from 100 to 150 nm or in the range from 150 to 200 nm or in the range from 200 to 250 nm.

The diameters of the primary particles as described for the purposes of the present invention can be determined, for example, by the electron-microscopic methods SEM (scanning electron microscopy) and TEM (transmission electron microscopy). The diameters described in the description of the present invention were determined by SEM.

The molar ratio of Si to Al in the zeolitic material is preferably in the range from 100 to 5000, more preferably in the range from 250 to 1500, more preferably in the range from 250 to 750 and particularly preferably in the range from 350 to 550.

The preferred crystalline zeolitic material, in particular of the structure type ZSM-5, has a monodisperse particle size distribution, with the coefficient of variation being less than 50%, preferably less than 25%, in particular less than 10%.

The particle size distribution is determined by laser light scattering in accordance with DIN 13320.

The specific surface area of the preferred crystalline zeolitic material, determined in accordance with DIN 66131 (BET), is preferably at least 350 m²/g and particularly preferably at least 400 m²/g. For example, the specific surface area is in the range from 350 to 500 m²/g and in particular in the range from 400 to 500 m²/g.

The pore volume of the preferred crystalline zeolitic material, determined in accordance with DIN 66134 (Langmuir; $p/p_o=0.9995$), is preferably at least 0.6 ml/g, particularly preferably at least 0.7 ml/g and very particularly preferably at least 0.8 ml/g. For example, the pore volume is in the range from 0.6 to 1.5 ml/g, more preferably in the range from 0.7 to 1.4 ml/g and particularly preferably in the range from 0.8 to 1.3 ml/g.

The preferred zeolitic material can generally be prepared by all suitable methods which are known to those skilled in the art and lead to the above-specified zeolitic material of the pentasil structure type, particularly preferably the ZSM-5 structure type.

High-silica ZSM-5 powders are commercially available, for example under the names TZP-9022 (Tricat Zeolites), CBV-28014 (Zeolyst International), T4573 (Südchemie), SN-300 (AlsiPenta), PZ-2/900 (Uetikon) and P400 (UOP).

The Solvent (Step I)

Suitable solvents are, for example, acyclic or cyclic ethers having from 2 to 12 carbon atoms, e.g. diethyl ether, di-n-propyl ether or its isomers, MTBE, THF, pyran, or lactones such as gamma-butyrolactone, polyethers such as monoglyme, diglyme, etc., aromatic or aliphatic hydrocarbons such as benzene, toluene, xylene, pentane, cyclopentane, hexane and petroleum ether, or mixtures thereof and in particular also N-methylpyrrolidone (NMP) or water or aqueous organic solvents or diluents of the abovementioned type.

As solvent, which can also be a diluent, particular preference is given to using water.

Either Brönsted acids or Brönsted bases can be added to the water.

Suitable Brönsted acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

Suitable Brönsted bases are primary, secondary and tertiary alkylamines, ammonia and also their earth metal hydroxides, alkali metal hydroxides and alkaline earth metal hydroxides.

The proportion of Brönsted acids or Brönsted bases in the solvent (e.g. water) is in particular from 0.5 to 50% by weight, preferably from 1 to 25% by weight, particularly preferably from 1 to 10% by weight.

The addition of the solvent gives the mixture the correct consistency for further processing in the shaping step. The proportion of solvent is preferably in the range from 0.5 to 80% by weight, more preferably in the range from 1 to 50% by weight, more preferably in the range from 1 to 40% by weight and particularly preferably in the range form 1 to 30% by weight, in each case based on the total mass of the mixture prepared in step 1.

The Make-Up Aid (Step I)

In the preparation of the mixture in (I), at least one make-up aid (=organic additive) is added.

As additive (=make-up aid), it is possible to use all compounds suitable for this purpose. These are preferably organic, in particular hydrophilic, polymers such as cellulose, cellulose derivatives such as methylcellulose, starch such as potato starch, polyacrylates, polymethacrylates, polyvinyl alcohol, polyvinylpyrrolidone (PVP), polyisobutene (PIB) or polytetrahydrofuran (PTHF).

In particular, compounds which also act as pore formers can be used as make-up aids.

The make-up aid is preferably used as a solid.

The make-up aid is, in a particularly preferred embodiment of the process of the invention as described below, removed to an extent of at least 90% by weight by calcination in step 5.

The addition of the make-up aid gives the mixture the correct consistency for further processing in the shaping step. The proportion of make-up aid is preferably in the range from 0.5 to 80% by weight, more preferably in the range from 1 to 50% by weight, more preferably in the range from 1 to 40% by weight and particularly preferably in the range from 1 to 30% by weight, in each case based on the total mass of the mixture prepared in step I.

Pore Formers (Optional, Step I)

The mixture of binder, the microporous, in particular zeolitic, material, make-up aid and solvent prepared in step I can be admixed with at least one further compound for further processing and to form a plastic composition. Preference is here given to, inter alia, pore formers.

Pore formers which can be used in the process of the invention include all compounds which provide a particular pore size, a particular pore size distribution and/or particular pore volumes in the finished shaped body.

Preference is given to using polymers which are dispersible, suspendable and/or emulsifiable in water or in aqueous solvent mixtures as pore formers in the process of the invention. Preferred polymers are polymeric vinyl compounds such as polyalkylene oxides, e.g. polyethylene oxides, polystyrene, polyacrylates, polymethacrylates, polyolefins, polyamides and polyesters, carbohydrates such as cellulose or cellulose derivatives, for example methylcellulose, or sugar or natural fibers. Further suitable pore formers are pulp or graphite.

Preference is also given to acidic organic compounds which can be removed by calcination in step V, as described below. Compounds which may be mentioned here are carboxylic acids, in particular $C_{1-8}$-carboxylic acids such as formic acid, oxalic acid and/or citric acid. It is likewise possible to use two or more of these acidic compounds.

If pore formers are used in the preparation of the mixture in step I, the content of pore formers in the mixture prepared in step (I) is preferably in the range from 0.5 to 80% by weight, more preferably in the range from 1 to 50% by weight and particularly preferably in the range from 1 to 30% by weight, in each case based on the amount of microporous, in particular zeolitic, material in the mixture prepared in step (I).

Should it be desired for achieving the pore size distribution wanted, it is also possible to use a mixture of two or more pore formers.

The pore formers are, in a particularly preferred embodiment of the process of the invention described below, removed to an extent of at least 90% by weight by calcination in step V to give the porous shaped body. In a preferred embodiment of the process of the invention, shaped bodies having pore volumes determined in accordance with DIN 66134 in the range of at least 0.4 ml/g, preferably in the range from 0.4 to 1.0 ml/g and particularly preferably in the range from >0.4 ml/g to 0.8 ml/g, are obtained.

The specific surface area of the shaped body of the invention, determined in accordance with DIN 66131, is preferably at least 300 $m^2/g$ and in particular at least 350 $m^2/g$.

For example, the specific surface area is in the range from 300 to 500 $m^2/g$ and preferably in the range from 350 to 500 $m^2/g$.

Mixing and Densification (Step II)

The order of addition of the constituents for preparing the mixture in step (I) is not critical.

After the preparation of the mixture in step (I), the mixture is homogenized, e.g. for a period in the range from 10 to 180 minutes. The homogenization is particularly preferably carried out using, inter alia, kneaders, pan mills or extruders. On a relatively small scale, the mixture is preferably kneaded. On a larger, industrial scale, a pan mill is preferably used for homogenization.

The homogenization is preferably carried out at temperatures in the range from about 10° C. to the boiling point of the solvent and at atmospheric pressure or slightly superatmospheric pressure. At least one of the above-described compounds can then be added if appropriate. The mixture obtained in this way is homogenized, preferably kneaded, until an extrudable plastic mass has been formed.

The homogenized mixture is shaped in a subsequent step.

Shaping of the Densified Mixture to Give a Shaped Body (Step III)

To carry out this step, preference is given to methods in which shaping is carried out by extrusion in customary extruders, for example to form extrudates having a diameter preferably from 1 to 10 mm and particularly preferably from 2 to 5 mm. Such extrusion apparatuses are described, for example, in Ullmann's Enzyklopädie der Technischen Chemie, 4th Edition, Vol. 2, p. 295 ff., 1972.

Apart from the use of a screw extruder, preference is likewise given to using a ram extruder for shaping.

However, shaping can in principle be carried out using all known and/or suitable kneading and shaping apparatuses and processes. Mention may be made of, inter alia:
(i) briquetting, i.e. mechanical pressing with or without addition of additional binder material;
(ii) pelletizing, i.e. compacting by means of circular and/or rotating motion;
(iii) sintering, i.e. the material to be shaped is subjected to a thermal treatment.

For example, the shaping method can be selected from the following group, with combinations of at least two of these methods explicitly being included: briquetting by punch pressing, roller pressing, annular roller pressing, briquetting without binder; pelletizing, melting, spinning techniques, deposition, foaming, spray drying; firing in a shaft furnace, convection furnace, moving grate, rotary tube furnace, pan milling.

Compaction can take place at ambient pressure or at a pressure slightly above ambient pressure, for example in a pressure range from 1 bar to several hundred bar. Furthermore, compaction can take place at ambient temperature or at a temperature slightly above ambient temperature, for example in a temperature range from 20 to 300° C. If drying and/or firing is part of the shaping step, temperatures up to 1500° C. are conceivable. Finally, compaction can take place in the ambient atmosphere or in a controlled atmosphere. Controlled atmospheres are, for example, protected gas atmospheres, reducing and/or oxidizing atmospheres.

The shaped bodies produced according to the invention can have any shape. In particular, they can be, inter alia, spheres, oval shapes, cylinders or pellets.

For the purposes of the present invention, shaping is particularly preferably carried out by extrusion of the mixture obtained in step II, giving extrudates which are more preferably essentially cylindrical rods having a diameter in the range from 0.5 to 20 mm, preferably in the range from 1 to 10 mm.

The length:diameter ratio of the extrudates is, in particular, at least 2, preferably in the range from >2 to 20, particularly preferably in the range from 4 to 10.

Drying of the Shaped Body (Step IV)

For the purposes of the present invention, step (III) is preferably followed by at least one drying step. This at least one drying step is carried out at temperatures in the range of preferably from 80 to 160° C., in particular from 90 to 145° C. and particularly preferably from 100 to 130° C., with the drying time preferably being 6 hours or more, for example in the range from 6 to 24 hours. However, depending on the moisture content of the material to be dried, shorter drying times of, for example, about 1, 2, 3, 4 or 5 hours are also possible.

Before and/or after the drying step, the extrudate obtained in the preferred manner can, for example, be comminuted. In this case, granules or crushed material having a particle size in the range from 0.1 to 5 mm, in particular from 0.5 to 2 mm, are/is preferably obtained.

Calcination of the Shaped Body (Step V)

Step (IV) is followed by at least one calcination step. The calcination is carried out at temperatures in the range of preferably from 350 to 750° C., in particular form 450 to 600° C.

Calcination can be carried out under any suitable gas atmosphere, with preference being given to air and/or oxygen-depleted air.

The calcination in step (V) can also be carried out in the presence of hydrogen, nitrogen, helium, argon and/or steam or mixtures thereof.

Furthermore, the calcination is preferably carried out in a muffle furnace, a rotary tube furnace and/or a belt calcination furnace, with the calcination time preferably being 1 hour or more, for example in the range from 1 to 24 hours or in the range from 3 to 12 hours. For example, it is possible in the process of the invention to calcine the shaped body once, twice or a greater number of times for at least one hour in each case, for example for from 3 to 12 hours in each case, with the temperatures during a calcination step being able to remain constant or be altered continuously or discontinuously. If two or more calcinations are carried out, the calcination temperatures in the individual steps can be different or identical.

After the calcination step, the calcined material can be, for example, comminuted. In this case, granules or crushed material having a particle size in the range from 0.1 to 5 mm, in particular from 0.5 to 2 mm, are/is preferably obtained.

The shaped bodies obtained according to the invention have hardnesses which are preferably in the range from 2 to 150 N, particularly preferably in the range from 5 to 100 and very particularly preferably at least 10 N, e.g. in the range from 10 to 75 N.

The above-described hardness was, for the purposes of the present invention, determined on an apparatus from Zwick, model BZ2.5/TS1S, at an initial loading of 0.5 N, a preliminary advance rate of 10 mm/min and a subsequent test speed of 1.6 mm/min. The apparatus had a rotating plate in a fixed position and a freely movable punch with built-in cutter having a thickness of 0.3 mm. The movable punch with the cutter was connected to a load cell to record the force and during the measurement moved toward the fixed rotating plate on which the shaped catalyst body to be tested was located. The test apparatus was controlled via a computer which recorded and evaluated the measurement results. The values obtained are the mean of measurements on 10 shaped catalyst bodies in each case. The shaped catalyst bodies had a cylindrical geometry whose mean length was approximately 2 to 3 times the diameter and were loaded with increasing force by means of the cutter having a thickness of 0.3 mm until the shaped body had been cut through. The cutter was pressed onto the shaped body perpendicular to the longitudinal axis of the shaped body. The force required for this is the cutting hardness (unit N).

After the calcination (step V), the shaped body can optionally be treated with a concentrated or diluted Brönsted acid or a mixture of two or more Brönsted acids. Suitable acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

This treatment is carried out in the, optionally aqueous, liquid phase at a preferred temperature in the range from 10 to 120° C. for a preferred time in the range from 0.5 to 12 hours.

This at least one treatment with at least one Brönsted acid is preferably followed by at least one drying step and/or at least one calcination step which is in each case carried out under the above-described conditions.

In a further, preferred embodiment of the process of the invention, the catalyst extrudates can be subjected to a steam treatment to improve the hardness after which the catalyst extrudates are again dried at least once and/or calcined at least once. For example, after at least one drying step and at least one subsequent calcination step, the calcined shaped body is subjected to steam treatment and is subsequently once again dried at least once and/or calcined at least once.

Use of the Shaped Catalyst Bodies

The shaped body of the invention can be used generally in all processes or process steps known to those skilled in the art in which the properties of the shaped body and in particular of the microporous, in particular zeolitic, material present in the shaped body are desired.

The shaped body of the invention is very particularly preferably used as catalyst in chemical reactions.

The shaped body of the invention can, for example, be used in the preparation of epsilon-caprolactam from cyclohexanone oxime and the preparation of ethanolamines from ethylene oxide and ammonia.

Very particular preference is given to the use of the shaped body as catalyst in the selective synthesis of triethylenediamine (TEDA).

The present invention provides a process for the selective preparation of triethylenediamine or an alkyl-substituted derivative thereof by reaction of a starting material having at least one structural unit (I)

where $R^1$, $R^2$, $R^3$ and $R^4$ are each, independently of one another, a hydrogen atom or an alkyl group having from 1 to 4 carbon atoms and X is an oxygen or nitrogen atom.

Examples of such compounds are, inter alia, ethylenediamine (EDA), monoethanolamine, diethanolamine, triethanolamine, piperazine (PIP), diethylenetriamine, triethylenetetramine, tri(2-aminoethyl)amine, N-(2-aminoethyl)ethanolamine, morpholine, N-(2-hydroxyethyl)piperazine, N,N'-bis(2-hydroxyethyl)piperazine, N-(2-aminoethyl)piperazine and N,N'-bis(2-aminoethyl)piperazine.

The composition of the product mixture is influenced decisively by the choice of starting materials. In particular, the avoidance of the formation of by-products is, in addition to the availability of the starting materials, an important aspect in relation to the TEDA specification to be achieved in the work-up. In most cases, the synthesis is carried out so that only partial conversion of the starting material or materials used occurs in order to increase the TEDA selectivity. The disadvantage of the low yield is accepted because of the low amounts of undesirable by-products which can be achieved.

For the purposes of the present invention, it is preferably possible, for example, to prepare TEDA by using piperazine (PIP) as starting material. It is likewise possible to use ethylenediamine (EDA) as starting material. It is also possible to use a mixture of EDA and PIP as starting material.

The selective preparation of triethylenediamine is preferably carried out by reaction of a starting material comprising (A) x % by weight of piperazine and (B) y % by weight of ethylenediamine, where x+y=100 and $0 \leq x \leq 100$ and $0 \leq y \leq 100$, over the shaped body of the invention as catalyst.

The process of the invention can be carried out batchwise but is preferably carried out continuously.

The reaction of the invention can be carried out in the liquid phase but is preferably carried out in the gas phase.

The reaction is preferably carried out in the presence of at least one solvent or diluent.

Suitable solvents or diluents are, for example, acyclic or cyclic ethers having from 2 to 12 carbon atoms, e.g. dimethyl ether, diethyl ether, di-n-propyl ether or its isomers, MTBE, THF, pyran, or lactones such as gamma-butyrolactone, polyethers such as monoglyme, diglyme, etc., aromatic or aliphatic hydrocarbons such as benzene, toluene, xylene, pentane, cyclopentane, hexane and petroleum ether, or mixtures thereof and in particular also N-methylpyrrolidone (NMP) or water or aqueous organic solvents or diluents of the above-mentioned type. Ammonia is also suitable as solvent or diluent.

Particular preference is given to using water as solvent or diluent, in particular solvent.

When the reaction is carried out in the gas phase, inert gases such as nitrogen (e.g. beyond the saturation of the reactor feed) or argon are also suitable as diluents. The reaction is preferably carried out in the gas phase in the presence of ammonia.

The starting components or the reactor feed are advantageously preheated.

As reactors in which the process of the invention is carried out, it is possible to use stirred vessels, in particular tube reactors and shell-and-tube reactors.

The shaped zeolite body of the invention is preferably present in the reactor as a fixed bed.

The reaction in the liquid phase can, for example, be carried out in the suspension, downflow or upflow mode.

The preferred reaction in the gas phase can be carried out in a fluidized bed or preferably fixed bed of catalyst.

If piperazine (PIP) alone is used as starting material, preference is given to process conditions in which the reaction temperature is in the range from 300 to 450° C., particularly preferably in the range from 315 to 400° C. The pressure under which the reaction takes place is in this case in a range from 0.01 to 50 bar, preferably in the range from 0.5 to 20 bar and particularly preferably in the region of atmospheric pressure plus the pressure drop occurring on passage over the catalyst bed.

Piperazine is also particularly preferably used in admixture with water, more preferably using a feedstream comprising at least 5% by weight of water, preferably from 10 to 70% by weight of water and in particular from 20 to 70% by weight of water, in each case based on the total weight of the feedstream comprising piperazine and water.

If piperazine is used as sole starting material, preference is given to a WHSV (weight hourly space velocity) in the range from 0.01 to 5 g (PIP)/g(cat.)·h$^{-1}$, preferably in the range from 0.02 to 1 g (PIP)/g(cat.)·h$^{-1}$ and particularly preferably in the range from 0.05 to 0.8 g (PIP)/g(cat.)·h$^{-1}$.

If EDA alone is used as starting material, preference is given to process conditions in which the reaction temperature is in the range form 300 to 400° C., particularly preferably in the range from 315 to 375° C. The absolute pressure under which the reaction takes place is in this case in a range from 0.01 to 50 bar, preferably in the range from 0.5 to 20 bar and particularly preferably in the region of atmospheric pressure plus the pressure drop occurring on passage over the catalyst bed.

EDA is also particularly preferably used in admixture with water, more preferably using a feedstream comprising at least 5% by weight of water, preferably from 10 to 70% by weight of water and in particular from 20 to 70% by weight of water, in each case based on the total weight of the feedstream comprising EDA and water.

If EDA is used as sole starting material, preference is given to a WHSV (weight hourly space velocity) in the range from 0.01 to 5 g (EDA)/g(cat.)·h$^{-1}$, preferably in the range from 0.02 to 1 g (EDA)/g(cat.)·h$^{-1}$ and particularly preferably in the range from 0.05 to 0.8 g (EDA)/g(cat.)·h$^{-1}$.

If a mixture of PIP and EDA is used as starting material, the reaction is preferably carried out so that during continuous operation in the steady state from 10 to 50% by weight of water and from 90 to 50% by weight of starting material (sum of the percentages by weight of the two compounds PIP and EDA), more preferably from 30 to 50% by weight of water and from 70 to 50% by weight of starting material and particularly preferably from 40 to 50% by weight of water and from 60 to 50% by weight of starting material, are fed in with the proportion of PIP or of EDA being able to be reduced or increased if appropriate to increase or decrease the amount of EDA or of PIP.

In the above-described embodiment in which from 35 to 60% by weight, for example about 40% by weight, of EDA are added, the reaction in the steady state can be carried out so that EDA is converted essentially completely into TEDA and PIP, and PIP is removed from the product stream together with any intermediates and/or by-products additionally present, preferably by distillation, and is, if appropriate after at least one of these intermediates and/or by-products has been separated off, admixed with approximately the same amount of EDA and the resulting mixture comprising EDA and PIP is returned to the reaction.

This process variant is preferably carried out so that the net consumption of PIP tends to zero and consequently essentially no additional PIP is added during continuous operation.

In this way of carrying out the process, it has surprisingly been found that the amount of EDA carried out tends to zero. The fractionation of the output from the reactor is therefore particularly simple.

A particular advantage of the process is that intermediate fractions comprising both TEDA and PIP can be returned to the reaction.

If a mixture of EDA and PIP is used as starting material, preference is given to process conditions in which the reaction temperature is in the range form 300 to 450° C., preferably in the range from 310 to 370° C., particularly preferably in the range from 310 to 350° C. The absolute pressure under which the reaction takes place is in this case in a range from 0.1 to 10 bar, preferably in the range from 0.8 to 2 bar and particularly preferably in the region of atmospheric pressure plus the pressure drop occurring on passage over the catalyst bed.

If a mixture of EDA and PIP is used as starting material, preference is given to a WHSV (weight hourly space velocity) in the range from 0.05 to 6 g (starting material)/g(cat.)·h$^{-1}$, preferably in the range from 0.2 to 2 g (starting material)/g (cat.)·h$^{-1}$ and particularly preferably in the range from 0.3 to 1 g (starting material)/g(cat.)·h$^{-1}$.

The use of the shaped catalyst body of the invention results, inter alia, in a very long operating life of the catalyst being achieved. This is preferably in the range above 1000 hours, particularly preferably at least 1200 hours, more preferably at least 1400 hours, more preferably at least 1600 hours, more preferably at least 1800 hours and particularly preferably at least 2000 hours. At constant reaction parameters, no deterioration in the conversion in the reaction was observed during the operating times indicated above.

In a further embodiment of the process of the invention, the catalyst is, regardless of its shape, regenerated after use, e.g. after the activity and/or selectivity has decreased, by a process in which regeneration is effected by targeted burning-off of the deposits responsible for the deactivation. This is preferably carried out in an inert gas atmosphere comprising precisely defined amounts of substances which supply oxygen. Such a regeneration process is described, inter alia, in WO-A-98/55228 and DE-A1-197 23 949, whose relevant disclosure is hereby fully incorporated by reference into the present patent application.

After the regeneration, the activity and/or selectivity of the catalyst are increased compared to their state immediately prior to regeneration.

The zeolite catalyst used according to the invention which is to be regenerated is heated to a temperature in the range from 250° C. to 800° C., preferably from 400° C. to 550° C. and in particular from 425° C. to 500° C., in an atmosphere comprising from 0.1 to about 20 parts by volume of substances which supply oxygen, particularly preferably from 0.1 to 20 parts by volume of oxygen, either in the reaction apparatus (reactor) or in an external oven. Heating is preferably carried out at a heating rate of from 0.1° C./min. to 20° C./min., preferably from 0.3° C./min. to 15° C./min. and in particular from 0.5° C./min. to 10° C./min.

During this heating phase, the catalyst is heated to a temperature at which the usually organic deposits present there begin to decompose, while at the same time the temperature is regulated by the oxygen content and thus does not rise to such an extent that damage to the catalyst structure occurs. The slow increase in the temperature or the residence at low temperature achieved by setting the appropriate oxygen content and the appropriate heating power is an essential step for preventing local overheating of the catalyst in the case of high organic loadings of the catalyst to be regenerated.

When the temperature of the offgas stream at the reactor outlet drops despite increasing amounts of substances which supply oxygen in the gas stream and/or the concentration of oxygen in the output from the reactor increases to the value at the inlet, the burning-off of the organic deposits is complete. The duration of the treatment is preferably from 1 to 30 hours, more preferably from about 2 to about 20 hours and in particular from about 3 to about 10 hours.

The subsequent cooling of the catalyst which has been regenerated in this way is preferably carried out so that it does not cool too rapidly, since otherwise the mechanical strength of the catalyst can be adversely affected.

It can be necessary for the catalyst which has been regenerated by calcination as described above to be rinsed with water and/or dilute acids such as hydrochloric acid in order to remove any remaining inorganic contamination of the catalyst due to impurities in the starting materials (traces of alkali, etc.). The catalyst can subsequently be dried again and/or calcined again.

In a further embodiment of the process of the invention, the at least partly deactivated catalyst is washed with a solvent in the reactor or in an external reactor to remove desired products still adhering to it before it is heated in the regeneration procedure. This washing is carried out in such a way that the desired products adhering to the catalyst can be removed therefrom but the temperature and pressure are not so high that the usually organic deposits are likewise removed. The catalyst is preferably merely rinsed with a suitable solvent. Solvents suitable for this washing procedure are all solvents in which the respective reaction product dissolves readily. The amount of solvent utilized and the duration of the washing procedure are not critical. The washing procedure can be repeated a number of times and can be carried out at elevated temperature. When $CO_2$ is used as solvent, supercritical pressure is preferred; otherwise, the washing procedure can be carried out under atmospheric pressure or superatmospheric or supercritical pressure. After the washing procedure is complete, the catalyst is generally dried. Although the drying procedure is generally not critical, the drying temperature should not be too far above the boiling point of the solvent used for washing in order to avoid the sudden vaporization of the solvent in the pores, in particular in the micropores, since this, too, can lead to damage to the catalyst.

In a preferred embodiment of the preparative process, the continuous process of the invention for the synthesis of TEDA does not have to be interrupted during regeneration of the catalyst of the invention in order to increase the process throughput. This can be achieved by the use of at least two reactors which are connected in parallel and can be operated alternately.

The catalyst regeneration can be carried out by taking at least one of the reactors connected in parallel out of operation in the respective reaction state and regenerating the catalyst present in this reactor, so that at least one reactor is always available for reaction of the starting material or starting materials in each stage during the continuous process.

To improve the purity of the TEDA obtained according to the invention, it can be recrystallized from suitable solvents such as pentane or hexane. However, this is usually not necessary, since TEDA can be prepared in a purity of at least 95% by weight, preferably at least 96% by weight and particularly preferably at least 97% by weight, by the process of the invention.

In a particular embodiment, the process for preparing TEDA as defined in the claims is combined with the subsequent TEDA process of EP-A-1 070 717 (BASF AG).

In the case of this combination, TEDA is firstly prepared according to the claims. In the subsequent work-up of the TEDA (e.g. by distillation), which can have a plurality of stages, the TEDA is vaporized, preferably in the last work-up stage (in particular a distillation or rectification stage), and the gaseous TEDA obtained, for example, at the top or at a side offtake of the distillation column, which preferably has a purity of greater than 95% by weight, in particular greater than 97% by weight, is passed into a liquid solvent. This introduction of the gaseous TEDA directly into a liquid solvent will hereinafter also be referred to as "TEDA quench".

The introduction of the gaseous TEDA into the liquid solvent is carried out in a quenching apparatus, e.g. preferably in a falling film condenser (thin film condenser, trickle film condenser or falling stream condenser) or in a nozzle apparatus. Here, the gaseous TEDA can be conveyed in cocurrent with or in countercurrent to the liquid solvent. Introduction of the gaseous TEDA into the quench apparatus from above is advantageous. It is also advantageous for the liquid solvent to be fed in tangentially at the top of the falling film condenser or for the liquid solvent to be fed in through one or more nozzles in order to achieve complete wetting of the interior wall of the quenching apparatus.

The temperature in the TEDA quench is preferably set to from 20 to 100° C., particularly preferably from 30 to 60° C., by heating the solvent used and/or the quenching apparatus. The absolute pressure in the TEDA quench is preferably from 0.5 to 1.5 bar.

The quench is preferably carried out so that, depending on the type of solvent, solutions having a TEDA content of from about 1 to 50% by weight, preferably from 20 to 40% by weight, are initially obtained in the TEDA quench.

Pure TEDA of high quality is obtained by subsequent crystallization of the TEDA from the solution obtained in this way.

The liquid solvent is preferably selected from the group consisting of cyclic and acyclic hydrocarbons, chlorinated aliphatic hydrocarbons, aromatic hydrocarbons, alcohols, ketones, aliphatic carboxylic esters, aliphatic nitriles and ethers.

When a solution of pure TEDA which can be used, for example, as catalyst solution in the production of polyurethane foam is to be prepared by the above process combination, the solvent used for the TEDA quench is preferably an alcohol (e.g. ethylene glycol, 1,4-butanediol, preferably dipropylene glycol). The color number of a 33% strength by weight TEDA solution in dipropylene glycol obtained in this way is less than 150 APHA, in particular less than 100 APHA, very particularly preferably less than 50 APHA.

The color number of the solutions obtained in this way is generally stable on storage for more than 6 months, preferably more than 12 months and particularly preferably more than 24 months.

When pure (crystalline) TEDA is to be prepared by the above process combination, the solvent used for the TEDA quench is preferably an aliphatic hydrocarbon, in particular a saturated aliphatic hydrocarbon having from 5 to 8 carbon atoms (e.g. hexane, heptane, preferably pentane). The crystallization of the pure TEDA from the TEDA solution prepared according to the invention can be carried out by the methods known to those skilled in the art. The TEDA crystals obtained by a subsequent multistage or preferably single-stage crystallization are highly pure (purity of generally at least 99.5% by weight, in particular at least 99.8% by weight; PIP content less than 0.1% by weight, in particular less than 0.05% by weight; N-ethylpiperazine content less than 0.02% by weight, in particular less than 0.01% by weight) and the color number of a 33% strength by weight solution in dipropylene glycol is less than 50 APHA, in particular less than 30 APHA.

All APHA numbers are determined in accordance with DIN ISO 6271.

EXAMPLES

The preparation of H-ZSM-5 having spherical primary zeolite particles with a diameter of <0.2 µm was carried out as described in the earlier German patent application no. 10356184.6 of Dec. 2, 2003 (BASF AG).

The BET surface areas (m²/g) and the pore volumes (ml/g) were determined in accordance with the standards DIN 66131 and DIN 66134, respectively.

GC Analysis:
Column RX-5, 30 m; temperature program: 80° C.-5° C./min.-280° C., detector: FID, internal standard: N-methylpyrrolidone (NMP).

The determination/measurement of the cutting hardness was carried out as described in the earlier German patent application no. 10326137.0 of Jun. 6, 2003 (BASF (AG):

The cutting hardnesses were measured on an apparatus from Zwick (model: BZ2.5/TS1S; initial loading: 0.5 N, preliminary advance rate: 10 mm/min.; test speed: 1.6 mm/min.) and are the means of in each case 10 measured catalyst extrudates.

In detail, the cutting hardness was determined as follows (see also further above in the description):

Extrudates were loaded with increasing force by means of a cutter having a thickness of 0.3 mm until the extrudate had been cut through. The force required for this is the cutting hardness in N (newton). The determination was carried out on a testing apparatus from Zwick, Ulm, having a rotating plate in a fixed position and a freely movable, vertical punch with built-in cutter having a thickness of 0.3 mm. The movable punch with the cutter was connected to a load cell to record the force and during the measurement moved toward the fixed rotating plate on which the extrudate to be measured was located. The test apparatus was controlled via a computer which recorded and evaluated the measurement results. 10 straight, preferably crack-free extrudates having a mean length of from 2 to 3 times the diameter were taken from a well-mixed catalyst sample and their cutting hardnesses were determined and subsequently averaged.

C=conversion in % by weight based on the amount of ethylenediamine (EDA) and piperazine (PIP) used;
S=selectivity of the reaction to triethylenediamine (TEDA) based on —$CH_2$—$CH_2$— units from EDA and PIP reacted.

Example 1

Production of Catalyst A1

120 g of H-ZSM-5 (modulus 1000, particle size 2-3 µm) were densified together with 75 g of Ludox® AS40 (colloidal silica, 39.5% by weight solution in ammoniacal water), 6 g of methylcellulose and 44 ml of water at room temperature in a mechanical kneader. The paste was then placed in a ram extruder and extruded to form 2 mm extrudates. The extrudates were dried at 120° C. in a drying oven for 16 hours and subsequently calcined at 500° C. with the introduction of atmospheric oxygen in a muffle furnace for 5 hours.

The cutting hardness of the shaped catalyst bodies was 4 N, the BET surface area was 337 m²/g and the pore volume was 0.27 ml/g.

Example 2

Production of Catalyst A2

130 g of H-ZSM-5 (modulus 1000, particle size 2-3 µm) were densified together with 46 g of Silres® MSE100 (methylsilicone, 70% strength by weight solution in toluene), 6 g of methylcellulose and 55 ml of water at room temperature in a mechanical kneader. The paste was placed in a ram extruder and extruded to form 2 mm extrudates. The extrudates were then dried at 120° C. in a drying oven for 16 hours and subsequently calcined at 500° C. with introduction of atmospheric oxygen in a muffle furnace for 5 hours.

The cutting hardness of the shaped catalyst bodies was 21 N, the BET surface area was 388 m²/g and the pore volume was 0.23 ml/g.

Example 3

Production of Catalyst B1

133 g of H-ZSM-5 (modulus 1000, particle size 0.1-0.2 µm) were densified together with 83 g of Ludox® AS40

(colloidal silica, 39.5% by weight solution in ammoniacal water), 8 g of methylcellulose and 110 ml of water at room temperature in a mechanical kneader. The paste was then placed in a ram extruder and extruded to form 2 mm extrudates. The extrudates were dried at 120° C. in a drying oven for 16 hours and subsequently calcined at 500° C. with the introduction of atmospheric oxygen in a muffle furnace for 5 hours.

The cutting hardness of the shaped catalyst bodies was 3 N, the BET surface area was 353 m²/g and the pore volume was 0.62 ml/g.

Example 4

Production of Catalyst B2

128 g of H-ZSM-5 (modulus 1000, particle size 0.1-0.2 µm) were densified together with 46 g of Silres® MSE100 (methylsilicone, 70% strength by weight solution in toluene), 6 g of methylcellulose and 120 ml of water at room temperature in a mechanical kneader. The paste was placed in a ram extruder and extruded to form 2 mm extrudates. The extrudates were then dried at 120° C. in a drying oven for 16 hours and subsequently calcined at 500° C. with introduction of atmospheric oxygen in a muffle furnace for 5 hours.

The cutting hardness of the shaped catalyst bodies was 20 N, the BET surface area was 445 m²/g and the pore volume was 0.60 ml/g.

Test Example 1

Synthesis of TEDA Using Catalyst A1

For the catalytic preparation of triethylenediamine (TEDA), an oil-heated double-walled tube (I=100 cm, d6 mm) was charged with 20 ml of catalyst A1 (2 mm extrudates) and subsequently heated under an inert atmosphere to 350° C. The catalyst was then supplied at atmospheric pressure with a mixture of ethylenediamine (EDA), piperazine (PIP) and water in a weight ratio of 25:25:50 at a WHSV (weight hourly space velocity) of 1.0 g (feed)/g(cat.)·h (=0.5 g (starting material)/g(cat.)·h). After a running time of 95 hours, the output from the reactor was collected in a cooled receiver for a period of 15 minutes and the qualitative and quantitative composition of the products was determined by means of gas chromatography.

The conversion of EDA was 98% at a selectivity to TEDA of 90% (see table 1).

Test Example 2

Synthesis of TEDA Using Catalyst A2

The test was carried out in a manner analogous to test example 1 using the catalyst A2.
The conversion of EDA was 95% at a selectivity to TEDA of 88% (see table 1).

Test Example 3

Synthesis of TEDA Using Catalyst B1

The test was carried out in a manner analogous to test example 1 using the catalyst B1.
The conversion of EDA was 97% at a selectivity to TEDA of 93% (see table 1).

Test Example 4

Synthesis of TEDA Using Catalyst B2

The test was carried out in a manner analogous to test example 1 using the catalyst B2.
The conversion of EDA was 97% at a selectivity to TEDA of 95% (see table 1).

TABLE 1

Preparation of TEDA

| Cat. | SiO₂ binder | Particle size [µm] | Cutting hardness [N] | C (EDA) [%] | S (TEDA) [%] |
|------|-------------|--------------------|-----------------------|-------------|---------------|
| A1   | Ludox       | 2-3                | 4                     | 98          | 90            |
| A2   | Silres      | 2-3                | 21                    | 95          | 88            |
| B1   | Ludox       | 0.2-0.1            | 3                     | 97          | 93            |
| B2   | Silres      | 0.2-0.1            | 20                    | 97          | 95            |

C = conversion,
S = selectivity; composition of the reaction mixture in each case after 95 h The use of methylsilicone as $SiO_2$ binder significantly improves the mechanical stability of the shaped catalyst body compared to the use of colloidal silica as $SiO_2$ binder (comparison of A1 with A2 and of B1 with B2). In combination with a particle size of the ZSM-5 powder of less than or equal to 0.2 µm, shaping of the zeolite powder with the aid of a methylsilicone leads to a higher mechanical stability and a better TEDA selectivity while the activity remains the same (comparison of B1 with B2).

The invention claimed is:

1. A process for producing a shaped body comprising a crystalline aluminosilicate (=zeolitic material) and at least one silicon-containing binder, which comprises the steps
    (I) preparing a mixture comprising the microporous material, the binder, a make-up aid and a solvent,
    (II) mixing and densifying the mixture,
    (III) shaping the densified mixture to give a shaped body,
    (IV) drying the shaped body and
    (V) calcining the dried shaped body,
    wherein the binder used is an organosilicon compound and at least 90% by weight of the primary particles of the zeolitic material are spherical and at least 95% by weight of the spherical primary particles have a diameter of less than or equal to 1 µm.

2. The process according to claim 1, wherein the binder used is a silicone.

3. The process according to claim 1, wherein the binder used is a methylsilicone.

4. The process according to claim 1, wherein the binder used is a cyclic silicone of the formula [—SiO(OR)(R')—]$_x$ or a linear silicone of the formula RO—[SiO(OR)(R')—]$_x$—R or a mixture of these silicones, where R and R' are $C_{1-6}$-alkyl groups and x is from 2 to 50.

5. The process according to claim 1, wherein at least 80% by weight of the organosilicon compound is converted into finely divided $SiO_2$ by the calcination of the shaped bodies in (V) and the proportion by weight of the resulting finely divided $SiO_2$ in the shaped body is in the range from 5 to 50% by weight.

6. The process according to claim 5, wherein the proportion by weight of the finely divided $SiO_2$ formed in the shaped body is in the range from 10 to 40% by weight.

7. The process according to claim 1, wherein the calcination in (V) is carried out in the presence of air, hydrogen, nitrogen, helium, argon and/or steam or mixtures thereof.

8. The process according to claim 1, wherein the crystalline aluminosilicate is a zeolite of the pentasil type.

9. The process according to claim 8, wherein the zeolite has one of the structure types MFI, MEL or a mixed structure derived therefrom.

10. The process according to claim 1, wherein the molar ratio of Si to Al in the crystalline aluminosilicate is greater than 10.

11. The process according to claim 1, wherein the molar ratio of Si to Al in the crystalline aluminosilicate is in the range from 100 to 5000.

12. The process according to claim 1, wherein the molar ratio of Si to Al in the crystalline aluminosilicate is in the range from 250 to 750.

13. The process according to claim 1, wherein the total alkali metal and alkaline earth metal content of the crystalline aluminosilicate is not more than 150 ppm by weight.

14. The process according to claim 1, wherein the diameter of the spherical primary particles is in the range from 50 to 250 nm.

15. The process according to claim 1, wherein the zeolitic material has a specific surface area (in accordance with DIN 66131 (BET)) of at least 350 m²/g and contains pores having a pore volume of at least 0.6 ml/g (in accordance with DIN 66134 (Langmuir)).

16. The process according to claim 1, wherein the solvent used in (I) is water.

17. The process according to claim 1, wherein the make-up aid used in (I) is cellulose, a cellulose derivative and/or a starch.

18. The process according to claim 1, wherein the mixture prepared in (I) further comprises at least one pore former.

19. The process according to claim 18, wherein the pore former is a polyalkylene oxide, polyacrylate, pulp and/or graphite.

20. The process according to claim 1, wherein the shaping in (III) is carried out by extrusion.

21. The process according to claim 20, wherein the diameter of the extrudates is in the range from 0.5 to 20 mm.

22. The process according to claim 1, wherein the calcination in (V) is carried out at a temperature in the range from 350 to 750° C. for a time in the range from 1 to 24 hours.

23. A shaped body which can be produced by a process according to claim 1.

24. The shaped body according to claim 23 which has a cutting hardness of at least 10 N.

25. The shaped body according to claim 23 which has a specific surface area (in accordance with DIN 66131 (BET)) of at least 300 m²/g and contains pores having a pore volume of at least 0.4 ml/g (in accordance with DIN 66134 (Langmuir)).

26. The shaped body according to claim 23, wherein the microporous material used is at least partly in the $H^+$ and/or $NH_4^+$ form.

27. A catalyst comprising the shaped body according to claim 23.

28. The catalyst according to claim 27, wherein the catalyst is used for the synthesis of triethylenediamine (TEDA).

29. A process for preparing triethylenediamine (TEDA) or an alkyl-substituted derivative thereof by reaction of a staffing material having at least one structural unit of the formula (I)

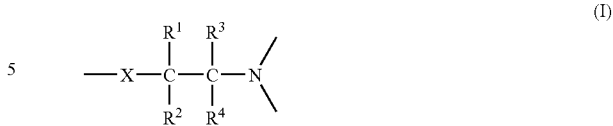

where $R^1$, $R^2$, $R^3$ and $R^4$ are each, independently of one another, a hydrogen atom or an alkyl group having from 1 to 4 carbon atoms and X is an oxygen or nitrogen atom, wherein the reaction is carried out over a shaped body according to claim 23 as catalyst.

30. The process according to claim 29, wherein the reaction is carried out continuously and in the gas phase.

31. The process according to claim 29, wherein ethylenediamine (EDA) and/or one or more amine compound(s) from the group consisting of monoethanolamine, diethanolamine, triethanolamine, piperazine (PIP), diethylenetriamine, triethylenetetramine, tri(2-aminoethyl)amine, morpholine, N-(2-aminoethyl)ethanolamine, N-(2-hydroxyethyl)piperazine, N-(2-aminoethyl)piperazine, N,N-bis(2-aminoethyl)piperazine, N,N-bis(2-hydroxyethyl)piperazine and N-(2-aminoethyl)-N'-(2-hydroxyethyl)piperazine are reacted as staffing material.

32. The process according to claim 29, wherein EDA and PIP in a weight ratio of x piperazine (PIP): y ethylenediamine (EDA), where x+y=100 and $0 \leq x \leq 100$ and $0 \leq y \leq 100$, are reacted as staffing material.

33. The process according to claim 29, wherein the starting material is reacted in at least one solvent or diluent.

34. The process according to claim 33, wherein the solvent or diluent is water and/or ammonia.

35. The process according to claim 33, wherein the weight ratio of staffing material: solvent or diluent is in the range from 95:5 to 5:95.

36. The process according to claim 29, wherein the reaction is carried out at a temperature in the range from 300 to 450° C. and an absolute pressure in the range from 0.01 to 50 bar.

37. The process according to claim 32, wherein x is 0.

38. The process according to claim 32, wherein y is 0.

39. The process according to claim 32, wherein x is in the range from 5 to 95.

40. The process according to claim 29, wherein the WHSV (weight hourly space velocity) is in the range from 0.05 to 10.0 g (staffing material)/g(cat).h.

41. A process for producing a shaped body comprising a material comprising at least one element from the group consisting of crystalline silicates, crystalline silicoaluminophosphates and at least one silicon-comprising binder, which comprises the steps
(I) preparing a mixture comprising the microporous material, the binder, a make-up aid and a solvent,
(II) mixing and densifying the mixture,
(III) shaping the densified mixture to give a shaped body,
(IV) drying the shaped body and
(V) calcining the dried shaped body,
wherein the binder used is an organosilicon compound.

* * * * *